United States Patent
Padilla-Acevedo

(10) Patent No.: US 11,292,757 B2
(45) Date of Patent: Apr. 5, 2022

(54) SYNTHESIS OF CYCLOPENTENONES

(71) Applicant: Dow Global Technologies LLC, Midland, MI (US)

(72) Inventor: Angela I. Padilla-Acevedo, Lake Jackson, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 17/263,183

(22) PCT Filed: Sep. 11, 2019

(86) PCT No.: PCT/US2019/050544
§ 371 (c)(1),
(2) Date: Jan. 26, 2021

(87) PCT Pub. No.: WO2020/068419
PCT Pub. Date: Apr. 2, 2020

(65) Prior Publication Data
US 2021/0206709 A1 Jul. 8, 2021

Related U.S. Application Data

(60) Provisional application No. 62/737,969, filed on Sep. 28, 2018.

(51) Int. Cl.
*C07C 45/67* (2006.01)

(52) U.S. Cl.
CPC .................................. *C07C 45/676* (2013.01)

(58) Field of Classification Search
CPC .............................. C07C 45/67; C07C 45/676
See application file for complete search history.

(56) References Cited

U.S. PATENT DOCUMENTS

| | | |
|---|---|---|
| 5,721,185 A | 2/1998 | LaPointe et al. |
| 8,785,677 B1 | 7/2014 | Narula et al. |
| 2004/0249096 A1 | 12/2004 | McCullough |
| 2020/0223881 A1 | 7/2020 | Padilla-Acevedo et al. |
| 2020/0277320 A1 | 9/2020 | Padilla-Acevedo et al. |

FOREIGN PATENT DOCUMENTS

| | | |
|---|---|---|
| EP | 0693506 | 1/1996 |
| EP | 0780395 | 6/1997 |
| JP | 10316694 | 12/1998 |
| WO | 2019/067272 | 4/2019 |
| WO | 2019067271 | 4/2019 |
| WO | 2019067273 | 4/2019 |

OTHER PUBLICATIONS

Austin et al., Journal of Organometallic Chemistry, 1995, p. 11-18, vol. 491.
Brancaccio and Lettieri, Farmaco Ed. Sc, 1983, p. 702-708, vol. 38.
Braude et al., Journal of the Chemical Society, 1953, p. 2208-2216.
Cheney and Paquette, J. Org. Chem., 1989, p. 3334-3347, vol. 54.
Conia, Tetrahedron Letters, 1968, p. 2101-2104, No. 17.
Dixon, "Phosphorus(V) Oxide-Methanesulfonic Acid", In Encyclopedia of Reagents for Organic Synthesis, (Ed.). , 2001, p. 1-4.
Eaton EL al., Journal of Org. Chem., 1978, p. 4071-4073, vol. 38, No. 23.
Farcasiu An Cao, Journal of Molecular Catalysis, 1994, p. 215-222, vol. 87.
Ouellette, J.Org. Chem., 1966, p. 3065-3067.
Paquette and Stevens, J. Chem., 1984, p. 2415-2420, vol. 62.
PCT/US2019/050544, International Search Report and Written Opinion dated Nov. 25, 2019.
PCT/US2019/050546, International Search Report and Written Opinion dated Nov. 29, 2019.
Rand and Dolinski, J. Org. Chem., 1966, p. 4061-4067, vol. 31.
Rand and Dolinski, J. Org. Chem.,1966, p. 3063-3065, vol. 31.
Tabatabaenian et al.,, Russian Journal of Coordination Chemistry, 2003, p. 501-504, vol. 29, No. 7.
Yang and Jensen, Novel and efficient synthesis of bis(eta.5-tetrahydroindenyl) dichlorides of titanium, zirconium and hafnium, 1996, p. 563-564, vol. 6.
Yokota et al., Journal of Polymer Science, 2005, p. 5041-5048, vol. 43.
Yoshio et al., Journal of Analytical and Applied Pyrolysis, 1989, p. 331-344.
Yoshio, 1986, p. 225-230, vol. 49.

*Primary Examiner* — Sikarl A Witherspoon

(57) ABSTRACT

A method comprising synthesizing a substituted cyclopentenone compound via reaction of a substituted cycloalkyl acrylate ester in the presence of phosphorous pentoxide/methanesulfonic acid reagent to make the substituted cyclopentenone compound.

5 Claims, No Drawings

SYNTHESIS OF CYCLOPENTENONES

FIELD

Synthesizing cyclopentenones.

INTRODUCTION

Uemichi, Yoshio; Kanoh, Hisao. *Kenkyu Hokoku-Asahi Garasu Kogyo Gijutsu Shoreikai*, Volume 49, Pages 225-30, 1986. CODEN:AGKGAA. ISSN:0365-2599 report that platinum is especially potent source of polyethylene degradation. Uemichi, Yoshio; Makino, Yutaka; Kanazuka, Takaji, *Degradation of polyethylene to aromatic hydrocarbons over metal-supported activated carbon catalysts*, Journal of Analytical and Applied Pyrolysis (1989), 14(4), 331-44.

See also the following. Tabatabaenian, K.; Mamaghani, M.; Neshat, A.; Masjedi, M. Synthesis and Spectroscopic Studies of New Substituted Dinuclear $\eta^5$-4,5,6,7-Tetrahydroindenyl Ruthenium Complexes. *Russian Journal of Coordination Chemistry.* 2003, 29, 7, 501. Austin, R. N.; Clark, T. J.; Dickson, T. E.; Killian, C. M.; Nile, T. A.; Shabacker, D. J.; McPhail, T. A. Synthesis and Properties of Novel Substituted 4,5,6,7-tetrahydroindenes and Selected Metal Complexes. *Journal of Organometallic Chemistry.* 1995, 491, 11. Conia, J. M.; Leriverend, M. L. *Tetrahedron Letters.* 1968, 17. 2101 (Conia et al.). L. Rand and R. J. Dolinski, *J. Org. Chem.,* 1966, 31, 3063 and L. Rand and R. J. Dolinski, *J. Org. Chem.,* 1966, 31, 4061 (collectively "Rand and Dolinski"). Yokota, K.; Kohsaka, T.; Ito, K.; Ishihara, N. Consideration of Mechanism of Styrene/Ethylene Copolymerization with Half-Titanocene Catalysts. *Journal of Polymer Science.* 2005, 43, 5041. JP10316694A to Tetsuya, I., et. al. Brancaccio G.; Lettieri, G.; Monforte, P.; Larizza, A. *Farmaco, Edizione Scientifica.* 1983, 9, 702-8. Eaton, P. E.; Carlson, G. R.; Lee, J. T. Phosphorus Pentoxide-Methanesulfonic Acid. A Convenient Alternative to Polyphosphoric Acid. *J. Org. Chem.* 1978, 38, 4071. Paquette, L. A.; Stevens, K. E., *Can. J. Chem.* 1984, 62, 2415. Paquette, L. A.; Cheney, D. L., *J. Org. Chem.* 1989, 54, 3334. *J. Org. Chem.* 1966, 3065.

Conia, et al. reported that reacting cyclohexene and crotonic acid in presence of polyphosphoric acid (PPA) exclusively gave as a sole product 2,3,4,5,6,7-hexahydro-3-methyl-1H-inden-1-one (structure 1 in Conia et al.). Conia et al. reported reacting cyclopentyl crotonate or cyclohexyl crotonate in the presence of PPA gave 3-methyl-bicyclo [3.3.0]-2-octen-1-one (40% yield, Table 1 in Conia et al.) or 2,3,4,5,6,7-hexahydro-3-methyl-1H-inden-1-one (60% yield, Table 2 in Conia et al.), respectively.

Rand and Dolinski report that using polyphosphoric acid (PPA) or a mixture of phosphorous pentoxide ($P_2O_5$ or $P_4O_{10}$) and PPA to catalyze the reaction of a cycloheptene, cyclohexene, or cyclopentene with an alpha,beta-unsaturated carboxylic acid such as acrylic acid or crotonic acid gives a reaction mixture that contains or is free of an ester by-product such as cycloheptyl crotonate, cyclohexyl crotonate, or cyclopentyl crotonate. Relatively how much of the ester by-product is made is said to depend on the amount of phosphorous pentoxide used in the mixture with PPA or the amount of the PPA or $P_2O_5$/PPA mixture relative to the amount of cycloalkene.

SUMMARY

The present invention includes a method of cyclizing, in the presence of a phosphorous pentoxide/methanesulfonic acid reagent (e.g., Eaton's reagent), an alpha,beta-unsaturated carboxylic acid, cycloalkyl ester compound to make a substituted cyclopentenone compound. The synthesis may be run at a lower temperature and yet be higher yielding than a prior PPA-based synthesis of Conia et al.

The substituted cyclopentenone compound made by the method may be used as an intermediate in the synthesis of compounds useful as drugs, herbicides, pesticides, or catalysts such as olefin polymerization catalysts such as substituted metallocene compounds.

DETAILED DESCRIPTION

The Summary and Abstract are incorporated here by reference.

Certain inventive embodiments are described below as numbered aspects for easy cross-referencing. Additional embodiments are described elsewhere herein.

Aspect 1. A method of synthesizing a substituted cyclopentenone compound, the method comprising (A) contacting a compound of formula (1) ("compound (1)"):

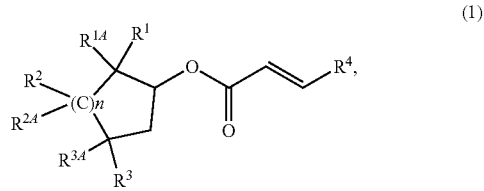

(1)

wherein subscript n is 1, 2, 3, or 4; and each of groups R1, R2, R3, and R4 is independently H or ($C_1$-$C_4$)alkyl, or any two adjacent R1 to R3 groups are bonded together to form a ($C_1$-$C_4$)alkylene and the remaining group of R1 to R3 is H or ($C_1$-$C_4$)alkyl, with an effective amount of a phosphorous pentoxide/methanesulfonic acid reagent ($P_2O_5$/$H_3CSO_3H$ reagent) and under reaction conditions sufficient to make a compound of formula (2) ("compound (2)"):

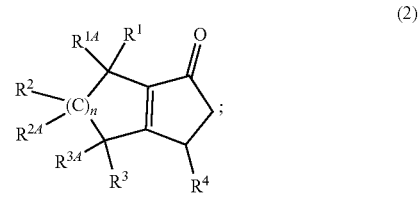

(2)

wherein subscript n and groups R1 to R4 are as defined above; and with the proviso that the contacting step (A) is free of a polyphosphoric acid (PPA). The reaction conditions sufficient to make compound (2) include an anhydrous environment and a temperature from −80° to 30° C. Step (A) may be free of PPA.

Aspect 2. The method of aspect 1 wherein the ratio of $P_2O_5$ to $H_3CSO_3H$ used to make the $P_2O_5$/$H_3CSO_3H$ reagent is from 0.05/1 to 1/1 (weight/weight).

Aspect 3. The method of aspect 1 or 2, wherein the ratio of $P_2O_5$ to $H_3CSO_3H$ used to make the $P_2O_5$/$H_3CSO_3H$ reagent is 0.1/1 (weight/weight). Known as Eaton's reagent.

Aspect 4. The method of any one of aspects 1 to 3, characterized by any one of limitations (i) to (xxi): (i) wherein at least one of R1 to R3 is a ($C_1$-$C_4$)alkyl or R4 is H; (ii) wherein each of R1 to R4 is H; (iii) wherein each of R1 to R3 is H and R4 is methyl; (iv) wherein each of R1 and R2 is H and each of R3 and R4 is methyl; (v) wherein R1 and/or R2 is methyl and R3 is H; (vi) wherein R1 is methyl, R2 is 1-methylethyl (i.e., isopropyl), and R3 is H; (vii) wherein R1 is 1-methylethyl (i.e., isopropyl), R2 is methyl, and R3 is H; (viii) wherein R1 and R2 independently are $(C_1$-$C_4)$alkyl, R3 is H, and the stereochemistry of the carbon atom bonded to R1 is (R) and the stereochemistry to the carbon atom bonded to R2 is (S); (ix) wherein R1 and R2 independently are $(C_1$-$C_4)$alkyl, R3 is H, and the stereochemistry of the carbon atom bonded to R1 is (S) and the stereochemistry to the carbon atom bonded to R2 is (R); (x) both (vi) and (viii); (xi) both (vi) and (ix); (xii) both (vii) and (viii); (xiii) both (vii) and (ix); (xiv) wherein R5 is H; (xv) wherein R5 is methyl; (xvi) both (i) and (xiv) or (xv); (xvii) both (ii) and (xiv) or (xv); (xviii) both (iii) and (xiv) or (xv); (xix) both (iv) and (xiv) or (xv); (xx) both (v) and (xiv) or (xv); and (xxi) any two adjacent R1 to R3 groups are bonded together to form a $(C_1$-$C_4)$alkylene and the remaining group of R1 to R3 is H or $(C_1$-$C_4)$alkyl.

Aspect 5. The method of any one of aspects 1 to 4, wherein the compound (2) is selected from the group consisting of any one of compounds (2a) to (2e): compound (2a) 2,3,4,5,6,7-hexahydro-3-methyl-1H-inden-1-one, having structure (2a):

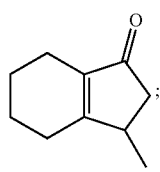

(2a)

compound (2b) bicyclo[3.3.0]-1(5)-octen-2-one, having structure (2b):

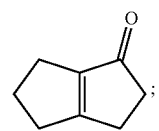

(2b)

compound (2c) 4-methyl-bicyclo[3.3.0]-1(5)-octen-2-one, having structure (2c):

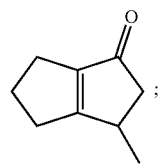

(2c)

compound (2d) 10-methyl-bicyclo[5.3.0]-1(7)-decen-8-one; and compound (2e) 2,4,6,11-tetramethyl-bicyclo[6.3.0]-1(8)-undecen-9-one.

The compound (2) may be free of platinum, palladium, nickel, rhodium, and ruthenium. The compound (2) may be used as an intermediate in the synthesis of compounds useful as drugs, herbicides, pesticides, or catalysts such as olefin polymerization catalysts such as substituted metallocene compounds. For example, the compound (2) may be converted to a substituted cyclopentadiene compound by reducing the carbonyl group (C=O) of compound (2) to an alcohol, and dehydrating the alcohol to give the substituted cyclopentadiene compound. The substituted cyclopentadiene compound may be deprotonated with a strong base such as an alkyl lithium to give a substituted cyclopentadienyl anion, one or two or which may be complexed with a transition metal such as a Group 4 metal (e.g., Ti, Zr, or Hf) to give a substituted metallocene compound comprising a metal-(substituted cyclopentadienyl ligand) complex. The substituted metallocene compound may be used as an olefin polymerization catalyst or may be activated with an activator (e.g., a trialkylaluminum) to give a substituted metallocene catalyst for polymerizing olefin monomers such as ethylene and alpha-olefins.

The term "free of" means contains no detectable presence of.

As subscript n and groups R1 to R4 are defined for compound (1), so they may be defined for compound (2).

Compound (1) may be obtained from a commercial supplier or synthesized from starting materials suitable for making alpha,beta-unsaturated carboxylic acid, cycloalkyl esters. Examples of commercially available compound (1) are (1a) (2E)-2-butenoic acid, cyclohexyl ester; (1b) (2E)-2-butenoic acid, cyclopentyl ester (CAS 1195328-04-1); (1c) (2E)-2-butenoic acid, cycloheptyl ester (CAS 10555-39-2); and (1d) propenoic acid, cyclopentyl ester (CAS 16868-13-6). (2E)-2-butenoic acid is also known as (E)-crotonic acid. Unless stated otherwise herein, "crotonic acid" means (2E)-2-butenoic acid. In some embodiments compound (1) is any one of compounds (1a) to (1d), alternatively compound (1) is selected from the group consisting of any three of compounds (1a) to (1d); alternatively compound (1) is compound (1a), alternatively compound (1b), alternatively compound (1c), alternatively compound (1d).

Compound (1) may be readily synthesized by reacting a corresponding cycloalkanol of formula (a):

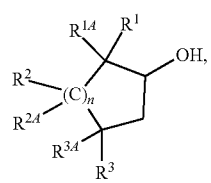

(a)

wherein subscript n and groups R1 to R3 are as defined for compound (1), with an alpha,beta-unsaturated carboxylic acid of formula (b):

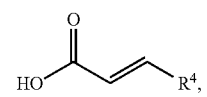

(b)

wherein R4 is as defined for compound (1), under dehydrating conditions. Suitable dehydrating conditions include refluxing toluene, a protic acid such as para-toluenesulfonic acid (pTsOH), and a Dean-Stark trap for removing, or a drying agent for sequestering, water that is generated. Examples of drying agent are 3 Ångström molecular sieves and anhydrous sodium sulfate. Methods and conditions for synthesizing carboxylic esters from the corresponding alcohol and carboxylic acid are well-known and useful. The compound (1) may also be synthesized by reacting the cycloalkanol of formula (a) with a corresponding alpha,beta-unsaturated carboxylic anhydride, which may be made by dehydrating two mole equivalents of compound (b).

Cycloalkanol compound (a) may be obtained from commercial suppliers or synthesized by well-known methods of making alcohols. Examples of commercially available compounds (a) wherein subscript n is 1 are (a1) cyclopentanol (CAS 96-41-3); (a2) 3-methyl-cyclopentanol (CAS 18729-48-1); (a3) 3,4-dimethyl-cyclopentanol (CAS 73316-51-5); and (a4) 3,3-dimethyl-cyclopentanol (CAS 60670-47-5). Examples of commercially available compounds (a) wherein subscript n is 2 are (a5) cyclohexanol (CAS 108-93-0); (a6) 2-methylcyclohexanol (mixture of stereoisomers or single enantiomers); (a7) 4-methylcyclohexanol (CAS 589-91-3); (a8) 2,5-dimethylcyclohexanol (CAS 3809-32-3); and (A9) 5-methyl-2-(1-methylethyl)-cyclohexanol (e.g., as a mixture of stereoisomers or as any one single enantiomer thereof such as (1R,2S,5R)-menthol). Examples of commercially available compounds (a) wherein subscript n is 3 are (a10) cycloheptanol (CAS 502-41-0); (a11) 4-methylcycloheptanol (CAS 90200-61-6); and (a12) 4,4-dimethylcycloheptanol (CAS 35099-84-4). Examples of commercially available compounds (a) wherein subscript n is 4 are (a13) cyclooctanol (CAS 696-71-9); and (a14) 3,5,7-trimethylcyclooctanol (CAS 1823711-29-0). In some embodiments compound (1) is made from, and the alcohol-derived portion containing R1-R3 corresponds to, any one of compounds (a1) to (a14), alternatively a compound selected from the group consisting of any thirteen of compounds (a1) to (a14), alternatively a compound (1) wherein subscript n is 1, 2, or 3; alternatively a compound (1) wherein subscript n is 1 or 2; alternatively a compound (1) wherein subscript n is 1; alternatively a compound (1) wherein subscript n is 2; alternatively a compound (1) wherein subscript n is 3 or 4; alternatively a compound (1) wherein subscript n is 3; alternatively a compound (1) wherein subscript n is 4.

Alpha,beta-unsaturated carboxylic acid compound (b) may be obtained from commercial suppliers or synthesized by well-known methods of making carboxylic acids. Examples of commercially available compounds (b) are (b1) acrylic acid (compound (b) wherein R4 is H); (b2) crotonic acid (compound (b) wherein R4 is methyl); (b3) 2-pentenoic acid (compound (b) wherein R4 is ethyl); and (b4) 2-hexenoic acid (compound (b) wherein R4 is propyl). In some embodiments compound (1) is made from, and the carboxylic acid-derived portion containing R4 corresponds to, any one of compounds (b1) to (b4); alternatively a compound selected from the group consisting of any three of compounds (b1) to (b4); alternatively compound (b1) or (b2); alternatively compound (b1); alternatively compound (b2); alternatively compound (b3) or (b4); alternatively compound (b3); alternatively compound (b4).

Alkyl means an unsubstituted univalent saturated acyclic hydrocarbon that is straight chain (1 or more carbon atoms), branched chain (if 3 or more carbon atoms), or cyclic (if 3 or more carbon atoms). Each $(C_1-C_4)$alkyl is independently methyl, ethyl, propyl, 1-methylethyl, butyl, 1-methylpropyl, 2-methylpropyl, or 1,1-dimethylethyl. Alternatively each $(C_1-C_4)$alkyl is independently a $(C_1-C_3)$alkyl; alternatively a $(C_2-C_4)$alkyl; alternatively $(C_1-C_2)$alkyl; alternatively $(C_2-C_3)$alkyl; alternatively $(C_3-C_4)$alkyl; alternatively methyl or $(C_3)$alkyl. In some aspects each $(C_1-C_4)$alkyl is independently a $(C_1-C_3)$alkyl and each $(C_1-C_3)$alkyl is independently methyl, ethyl, propyl, or 1-methylethyl; alternatively methyl, propyl, or 1-methylethyl; alternatively methyl; alternatively ethyl; alternatively propyl; alternatively 1-methylethyl. Substituted alkyl is an alkyl as defined above except wherein one or more hydrogen atoms is formally replaced by a substituent such as unsubstituted alkyl, halogen, or alkylcarboxylic ester.

Alkylene is unsubstituted divalent saturated acyclic hydrocarbon that is straight chain (1 or more carbon atoms), branched chain (if 3 or more carbon atoms), or cyclic (if 3 or more carbon atoms). Each $(C_1-C_4)$alkylene is independently methylene $(CH_2)$, ethylene $(CH_2CH_2)$, propylene $(CH_2CH_2CH_2)$, 1-methylethylene $(CH(CH_3)CH_2)$, butylene $((CH_2)_4)$, 1-methylpropylene $(CH(CH_3)CH_2CH_2)$, 2-methylpropylene $(CH_2CH(CH_3)CH_2)$, or 1,1-dimethylethylene $(C(CH_3)_2CH_2)$. Substituted alkylene is an alkylene as defined above except wherein one or more hydrogen atoms is formally replaced by a substituent such as unsubstituted alkyl, halogen, or alkylcarboxylic ester.

Compound means a molecule or collection of molecules.

Effective amount is a quantity sufficient for enabling the making of a detectable amount of intended product (e.g., compound (2)). An effective amount of the phosphoric and/or sulfonic acid reagent is a quantity thereof sufficient for enabling the making of a detectable amount of compound (2). Detectable amounts may be characterized by any suitable analytical method such as 1H-nuclear magnetic resonance (1H-NMR), high performance liquid chromatography (HPLC, versus a known standard), gas chromatography (GC, versus a known standard), or mass spectrometry; typically 1H-NMR. The effective amount of the phosphorous pentoxide/methanesulfonic acid reagent used in step (A) may vary depending upon its composition, reaction conditions, and costs. A skilled person may determine an optimal effective amount thereof by starting with an initial reaction mixture of (1) and 95 wt % of the phosphorous pentoxide/methanesulfonic acid reagent, and thereafter systematically try reaction mixtures containing lower wt % of the phosphorous pentoxide/methanesulfonic acid reagent until an optimal result under the reaction conditions is found. The effective amount may be from 50 to 95 wt %, alternatively from 50 to 80 wt % based on total weight of (1) and the phosphorous pentoxide/methanesulfonic acid reagent. Alternatively, the effective amount of the $P_2O_5/H_3CSO_3H$ reagent may be from 1 to 10 mole equivalents (mol equiv.), alternatively 1 to 5 mol equiv., alternatively 1 to 3 mol equiv. relative to the number of moles of compound (1). E.g., if 1.0 mole of compound (1) is used in the contacting step (A), then the effective amount of the $P_2O_5/H_3CSO_3H$ reagent may be from 1 to 10 moles, alternatively 1 to 5 moles, alternatively 1 to 3 moles.

Methanesulfonic acid is a compound of formula $H_3CSO_3H$ and has CAS number 75-75-2 and is widely available from commercial suppliers.

Phosphorous pentoxide is a compound of formula $P_2O_5$ (also written as $P_4O_{10}$) and has CAS number 1314-56-3 and is widely available from commercial suppliers.

The phosphorous pentoxide and methanesulfonic acid reagent ("$P_2O_5/H_3CSO_3H$ reagent", also written as $P_4O_{10}/H_3CSO_3H$ reagent or $P_2O_5/MeSO_3H$ reagent) is a physical blend of $P_2O_5$ (also written as $P_4O_{10}$) and $H_3CSO_3H$, or a reaction product thereof. The weight/weight ratio of $P_2O_5/H_3CSO_3H$ in the reagent may be from 0.05/1 to 1/1, alternatively 0.1/1 to 1/1 alternatively 0.15/1 to 1/1, alternatively 0.2/1 to 1/1, alternatively 0.05/1 to 0.14/1, alternatively 0.1/1. The 0.1/1 (wt/wt) $P_2O_5/H_3CSO_3H$ reagent is commercially available and may be referred to as Eaton's reagent. The reagent of $P_2O_5$ and $CH_3SO_3H$ may be formed in situ in the presence of the compound (1), such as prior to or during the contacting step (A). Alternatively, the reagent of $P_2O_5$ and $CH_3SO_3H$ may be pre-formed (in absence of compound (1)) before contacting step (A). It is convenient to pre-form the $P_2O_5/CH_3SO_3H$ reagent before contacting step (A), and store the resulting preformed reagent for later use in embodiments of the contacting step (A). In some aspects the method further comprises limitation (i) or (ii): (i) a step of preforming the $P_2O_5/H_3CSO_3H$ reagent before the contacting step (A) and in the absence of compound (1); or (ii) wherein the contacting step further comprises contacting a phosphorous pentoxide and methanesulfonic acid together in the presence of compound (1) to form the $P_2O_5/H_3CSO_3H$ reagent in situ.

Polyphosphoric acid or PPA has CAS no. 8017-16-1 and is a compound generally of formula HO—[P(=O)(OH)]$_n$—H wherein subscript n indicates degree of polymerization. PPA consists of oxygen and phosphorous atoms and is free of sulfur and carbon atoms.

In some aspects each reactant, reagent, solvent, or other material used in the inventive methods, and each product thereof, is free of Pt, Ni, Pd, Rh, and Ru.

Under reaction conditions sufficient to make are included reaction temperature; reaction pressure; reaction atmosphere; reaction solvent, if any; reactant and reagent concentrations; molar ratios of reactants to each other and to reagents; and absence of negating compounds. Reaction pressure is typically room pressure (e.g., 101 kilopascals (kPa), except higher for olefin polymerization reactions. If desired reactions (e.g., step (A)) may be carried out in a fume hood under an anhydrous molecular nitrogen gas atmosphere or using Schlenck line techniques and conditions.

Reaction temperatures under reaction conditions sufficient to make may vary from step to step. For example, in step (A) (cyclization), the under reaction conditions sufficient to make compound (2) may include a reaction temperature of from −78° to 30° C., alternatively from −30° to 25° C., alternatively from 0° to 25° C., alternatively from −5° to 5° C.

The use or not of solvent and the type of solvent if used under reaction conditions sufficient to make may vary from step to step. Step (A) may be free of solvent or may employ a solvent. When the amount of the methanesulfonic acid is sufficient for solubilizing reactants, a solvent may be omitted. Alternatively, polar aprotic solvent may be employed. The polar aprotic solvent may be selected from sulfolane, 1,2-dimethoxyethane, 1-methoxy-2-(2-methoxyethoxy)ethane, and mixtures of any two or more thereof. The amount of polar aprotic solvent employed is not particularly important. The foregoing polar aprotic solvents may serve to solubilize the compound (1) and/or the $P_2O_5/H_3CSO_3H$ reagent. The amount of solvent employed may be sufficient to prepare a starting solution that is from 0.5 Molar (M) to 5 M, or 1 M to 2.5 M of $P_2O_5/H_3CSO_3H$ reagent therein. The polar aprotic solvent may allow the contacting step (A) to be performed at lower temperatures within the ranges given above therefor. A polar aprotic solvent is used for the $P_2O_5/H_3CSO_3H$ reagent because a protic solvent is expected to undesirably react with the $P_2O_5/H_3CSO_3H$ reagent, which is a powerful dehydrating agent. The polar aprotic solvent may be of intermediate polarity in order to co-solubilize the compound (1) and $P_2O_5/H_3CSO_3H$ reagent. The polar aprotic solvent may be capable of producing a homogeneous solution of the compound (1) at from −25° to 25° C., alternatively at 25° C., alternatively at 10° C., alternatively at 0° C., alternatively at −10° C., alternatively at −25° C. A homogeneous solution is not required for successful reaction of compound (1) in the presence of the $P_2O_5/H_3CSO_3H$ reagent.

Reaction atmosphere included under reaction conditions sufficient to make may be anhydrous molecular nitrogen gas or Schlenck line conditions for step (A) (cyclization)

Reaction concentrations of reactants and reagents included under reaction conditions sufficient to make may be independently in the range from 0.1 to 1.4 M, alternatively 0.25 to 1 Molar (M), alternatively 0.4 to 1 M.

Molar ratios of reactants to each other and to reagents included under reaction conditions sufficient to make may vary from 0.25 times to 1.5 times theoretical reaction stoichiometry, alternatively from 0.99 times to 1.2 times theoretical reaction stoichiometry, alternatively from 1.0 to 1.1 times theoretical reaction stoichiometry, depending upon the reactants and reagents used.

Negating agents should not be included under reaction conditions sufficient to make. In step (A) (cyclization), a negating agent may be a quantity of a basic compound that would neutralize the acidity of the $P_2O_5/H_3CSO_3H$ reagent or otherwise render it ineffective. For example, purity of compound (1) used in step (A) may be at least 95%, alternatively at least 98%, alternatively at least 99%, alternatively at least 99.5% by weight.

A compound includes all its isotopes and natural abundance and isotopically-enriched forms. The enriched forms may have medical or anti-counterfeiting uses.

In some aspects any compound, composition, formulation, mixture, or reaction product herein may be free of any one of the chemical elements selected from the group consisting of: H, Li, Be, B, C, N, O, F, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Tc, Ru, Rh, Pd, Ag, Cd, In, Sn, Sb, Te, I, Cs, Ba, Hf, Ta, W, Re, Os, Ir, Pt, Au, Hg, Tl, Pb, Bi, lanthanoids, and actinoids; with the proviso that chemical elements required by the compound, composition, formulation, mixture, or reaction product (e.g., C and H required by a polyolefin or C, H, and O required by an alcohol) are not excluded.

The following apply unless indicated otherwise. Alternatively precedes a distinct embodiment. ASTM means the standards organization, ASTM International, West Conshohocken, Pa., USA. Any comparative example is used for illustration purposes only and shall not be prior art. Free of or lacks means a complete absence of; alternatively not detectable. May confers a permitted choice, not an imperative. Operative means functionally capable or effective. Optional(ly) means is absent (excluded), alternatively is present (included). Properties are measured using a standard test method and conditions for the measuring (e.g., viscosity: 23° C. and 101.3 kPa). Ranges include endpoints, subranges, and whole and/or fractional values subsumed therein, except a range of integers does not include fractional values. Room temperature: 23° C.±1° C. Substituted when referring to a compound means having, in place of hydrogen, one or more substituents, up to and including per substitution. Any conflict between structure and name of a compound, the structure controls.

EXAMPLES

Unless noted otherwise herein, use the following preparations for characterizations. Carry out syntheses under an atmosphere of dry nitrogen in a glovebox when indicated. Perform reactions requiring anhydrous conditions under an atmosphere of dry nitrogen in oven-dried glassware cooled under a stream of dry nitrogen. Anhydrous toluene, hexanes, tetrahydrofuran, diethyl ether and 1,2-dimethoxyethane are from Sigma-Aldrich. Solvents that are used for experiments performed in a nitrogen-filled glovebox are further dried by storage over activated 4 Angstrom (Å) molecular sieves. All other reagents are purchased from Sigma-Aldrich and are used as received. For example, 0.1/1 (wt/wt) $P_2O_6/MeSO_3H$ reagent may be purchased from Sigma-Aldrich CAS #39394-84-8.

$^1$H-NMR (proton nuclear magnetic resonance spectroscopy) chemical shift data are reported in parts per million (ppm) down field relative to tetramethylsilane (TMS), δ scale, using residual protons in deuterated solvent as references. The $^1$H-NMR chemical shift data measured in $CDCl_3$ are referenced to 7.26 ppm, data measured in benzene-d6 ($C_6D_6$) to 7.16 ppm, data measured in tetrahydrofuran-d8 (THF-d8) to 3.58 ppm. $^1$H-NMR chemical shift data are reported in the format: chemical shift in ppm (multiplicity, coupling constant(s) in Hertz (Hz), and integration value. Multiplicities are abbreviated s (singlet), d (doublet), t (triplet), q (quartet), pent (pentet), m (multiplet), and br (broad). GC/MS (EI) means gas chromatography-mass spectrometry (electron ionization).

Preparation 1: synthesis of (1a) (2E)-2-butenoic acid, cyclohexyl ester

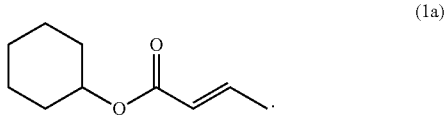

(1a)

In a fume hood, cyclohexanol (30 milliliters (mL), 283.9 millimoles (mmol)), crotonic acid (25.9 g, 300.98 mmol), p-toluene sulfonic acid (1.08 g, 5.68 mmol) and 40 mL of toluene were charged into a 250 mL round bottom flask. The flask was equipped with a Dean-Stark trap and a reflux condenser. The resulting reaction mixture was heated to reflux, and water that was generated was removed azeotropically. After refluxing for 18 hours, the reaction mixture was cooled to ambient temperature, and quenched with water (55 mL). The resulting organic layer was separated and washed with saturated aqueous $NaHCO_3$ (2×40 mL), then brine (30 mL), and then dried over magnesium sulfate and filtered. The solvent was removed under reduced pressure to give compound (1a) as a light yellow liquid (40.6 g) in 85% yield. $^1$HNMR (400 MHz, Chloroform-d) δ 6.93 (dq, 1H), 5.81 (dq, 1H), 4.84-4.73 (m, 1H), 1.92-1.80 (m, 4H), 1.77-1.64 (m, 3H), 1.59-1.12 (m, 6H) and GC/MS (EI) (Mass found=168, 87, 69) were consistent with (2E)-2-butenoic acid, cyclohexyl ester.

Preparation 2 (prophetic): synthesis of (1b) (2E)-2-butenoic acid, 3,5,7-trimethylcyclooctyl ester (1e). Replicate Preparation 1 except substitute 284 mmol of (a14) 3,5,7-trimethylcyclooctanol (CAS 1823711-29-0) for the cyclohexanol to give (2E)-2-butenoic acid, 3,5,7-trimethylcyclooctyl ester (1b).

Preparation 3: synthesis of (2E)-2-butenoic acid, cyclopentyl ester (1c)

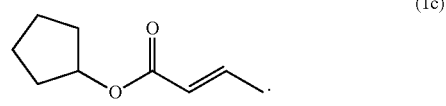

(1c)

In a fume hood, into a 50 mL round bottom flask equipped with a Dean-Stark trap and a reflux condenser, charge cyclopentanol (2.1 mL, 23.2 mmol), crotonic acid (2.11 g, 24.6 mmol), p-toluene sulfonic acid (0.088 g, 0.46 mmol), and 5 mL of toluene. Heat the resulting mixture to reflux, and remove generated water azeotropically. After refluxing for 18 hours, cool the reaction mixture to ambient temperature, and quench with water (10 mL). Separate the resulting organic layer, and wash it with saturated aqueous $NaHCO_3$ (2×10 mL), then brine (20 mL), and then dry over magnesium sulfate. Filter and remove solvent from the filtrate under reduced pressure to give 2.8 g (78% yield) of compound (1c) as a colorless liquid. $^1$HNMR and GC/MS (Mass found=154) were consistent with (2E)-2-butenoic acid, cyclopentyl ester. Compound (1c) is characterized by GC/MS (EI) 154 (mass), 87, 69. $^1$H NMR (400 MHz, Chloroform-d) δ 6.91 (dq, 1H), 5.79 (dq, 1H), 5.18 (tt, 1H), 1.94-1.79 (m, 5H), 1.83-1.63 (m, 4H), 1.67-1.48 (m, 2H).

Inventive Example 1: synthesis of compound (2a) 2,3,4,5,6,7-hexahydro-3-methyl-1-inden-1-one 1

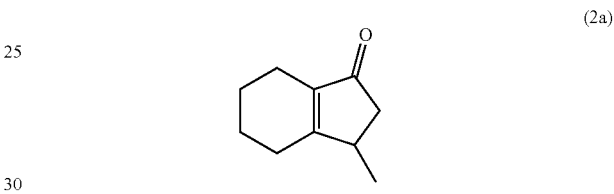

(2a)

(compound (2) wherein subscript n is 2, R1-R3 is H and R4 is methyl). In a fume hood, under a nitrogen atmosphere in a 250 mL round bottom flask equipped with a stir bar, added compound (1a) (2E)-2-butenoic acid, cyclohexyl ester (3 g, 17.8 mmol). Cooled the ester in the flask to 0° C. Then added dropwise $P_2O_5/H_3CSO_3H$ reagent (0.1/1)) (8.49 mL, 53.5 mmol) at 0° C. Warmed the resulting reaction mixture with stirring to ambient temperature (23° C.), and continued stirring for 72 hours at ambient temperature. Diluted the resulting crude product with 20 mL of water, then added solid $NaHCO_3$ in portions until bubbling subsided to give quenched mixture having pH 8 to pH 9. Separated aqueous and organic layers of quenched mixture in a separatory funnel. Extracted the aqueous layer three times with diethyl ether (3×20 mL). Combined the organic layer with the three extracts, and washed the combination with brine (30 mL), dried over magnesium sulfate, and filtered. Removed solvent in vacuo to give 2.45 g of compound (2a) as a light brown oil product (91.4% yield). $^1$HNMR (400 MHz, Chloroform-d) δ 2.77-2.67 (m, 1H), 2.61 (ddd, 1H), 2.48-2.34 (m, 1H), 2.32-2.03 (m, 3H), 2.03-1.47 (m, 5H), 1.14 (d, 3H) was consistent with (2a) 2,3,4,5,6,7-hexahydro-3-methyl-1H-inden-1-one.

Inventive Example 2 (prophetic): synthesis of compound (2b) bicyclo[3.3.0]-1(5)-octen-2-one

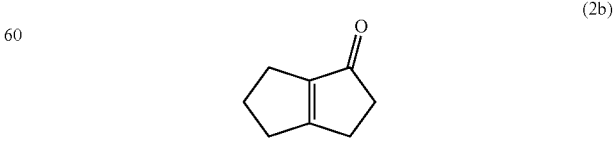

(2b)

(compound (2) wherein subscript n is 1 and R1-R4 are H). Replicate Inventive Example 1 except substitute 18 mmol of (1b) propenoic acid, cyclopentyl ester (CAS 16868-13-6) for compound (1a) to give compound (2b).

Inventive Example 3: synthesis of compound (2c) (4-methyl-bicyclo[3.3.0]-1(5)-octen-2-one, i.e., compound (2) wherein subscript n is 1 and R1-R3 are H and R4 is methyl):

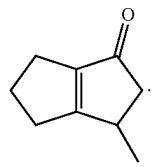

(2c)

In a fume hood, under a nitrogen atmosphere in a 100 mL round bottom flask equipped with a stir bar, added compound (1c) (2E)-2-butenoic acid, cyclopentyl ester (0.5 g, 3.24 mmol) of Preparation 3. Cooled the ester in the flask to 0° C. Then added dropwise $P_2O_5/H_3CSO_3H$ reagent (0.1/1)) (1.5 mL, 9.73 mmol) at 0° C. Warmed the resulting reaction mixture with stirring to ambient temperature (23° C.), and continued stirring for 72 hours. Diluted the resulting crude product with 5 mL of water, then added solid $NaHCO_3$ in portions until bubbling subsided to give quenched mixture having pH 8 to pH 9. Separated aqueous and organic layers of quenched mixture in a separatory funnel. Extracted the aqueous layer three times with diethyl ether (3×8 mL). Combined the organic layer with the three extracts, and washed the combination with brine (15 mL), dried over magnesium sulfate, and filtered. Removed solvent in vacuo to give 0.42 g (95% yield) of compound (2c) as an orange oil. $^1$H NMR (400 MHz, Chloroform-d) δ 3.05-2.89 (m, 1H), 2.81 (dt, 1H), 2.66-2.47 (m, 1H), 2.47-2.26 (m, 6H), 1.19 (d, 3H) was consistent with compound (2c).

Inventive Example 4 (prophetic): synthesis of compound (2d) 10-methyl-bicyclo[5.3.0]-1(7)-decen-8-one (compound (2) wherein subscript n is 3 and R1-R3 are H and R4 is methyl). Replicate Inventive Example 1 except substitute 18 mmol of (1c) (2E)-2-butenoic acid, cycloheptyl ester (CAS 10555-39-2) for compound (1a) to give compound (2d).

Inventive Example 5 (prophetic): synthesis of compound (2e) 2,4,6,11-tetramethyl-bicyclo[6.3.0]-1(8)-undecen-9-one (compound (2) wherein subscript n is 4 and R1-R4 are methyl). Replicate Inventive Example 1 except substitute 18 mmol of (1e) (2E)-2-butenoic acid, 3,5,7-trimethylcyclooctyl ester (Preparation 2) for compound (1a) to give compound (2e).

As discussed earlier, Conia et al., Rand and Dolinski, and others report using PPA or $P_2O_5$/PPA mixture to catalyze a reaction of cycloheptene, cyclohexene, or cyclopentene with an alpha,beta-unsaturated carboxylic acid such as acrylic acid or crotonic acid gives a reaction mixture that contains an ester by-product (e.g., cycloheptyl crotonate, cyclohexyl crotonate, or cyclopentyl crotonate, respectively). We found that using the phosphorous pentoxide/methanesulfonic acid reagent to catalyze a reaction of cycloheptene, cyclohexene, or cyclopentene with an alpha,beta-unsaturated carboxylic acid such as acrylic acid or crotonic acid gives a reaction mixture that does not contain an ester by-product (e.g., the reaction does not yield cycloheptyl crotonate, cyclohexyl crotonate, or cyclopentyl crotonate, respectively). We base this finding on analysis of at least one of the reaction mixtures by gas chromatography-mass spectrometry (GC-MS), which fails to show any ester by-product. We also base this finding on seeing that a reaction of cycloheptene, cyclohexene, or cyclopentene with an alpha,beta-unsaturated carboxylic acid such as acrylic acid or crotonic acid in the presence of the $P_2O_5/H_3CSO_3H$ reagent goes much faster than the reaction of cycloheptyl crotonate, cyclohexyl crotonate, or cyclopentyl crotonate, respectively, in the presence of the $P_2O_5/H_3CSO_3H$ reagent.

Without wishing to be bound by theory, we believe that the $P_2O_5/H_3CSO_3H$ reagent reacts with the alpha,beta-unsaturated carboxylic acid (e.g., crotonic acid) to give in situ a mixed anhydride of general formula R4CH=CHC(=O)—O—$SO_2$—$CH_3$, which generates in situ an acylium ion (i.e., acyl carbonium ion) of formula R4CH=CHC$^+$(=O), which rapidly undergoes a Friedel-Crafts acylation of cycloalkene to give in situ a ketone of formula $R^a$—C(=O)—$R^c$, wherein $R^a$ is R4CH=CH— and $R^c$ is cycloalken-1-yl, which ketone undergoes cyclization reaction to give the corresponding cyclopentenone. For example, when the cycloalkene is cyclohexene and the alpha,beta-unsaturated carboxylic acid is crotonic acid, we believe that the $P_2O_5/H_3CSO_3H$ reagent reacts with the crotonic acid to give in situ a mixed anhydride of general formula $H_3$CCH=CHC(=O)—O—$SO_2$—$CH_3$, which generates in situ an acylium ion (i.e., acyl carbonium ion) of formula $H_3$CCH=CHC$^+$(=O), which rapidly undergoes a Friedel-Crafts acylation of cycloalkene to give in situ a ketone of formula $R^a$—C(=O)—$R^c$, wherein $R^a$ is $H_3$CCH=CH— and $R^c$ is cyclohexen-1-yl which ketone undergoes cyclization reaction to give the corresponding cyclopentenone that is 2,3,4,5,6,7-hexahydro-3-methyl-1H-inden-1-one (i.e., 7-methyl-bicyclo[4.3.0]-7-nonen-9-one). Therefore, using the phosphorous pentoxide/methanesulfonic acid reagent in reaction of a cycloalkene such as cycloheptene, cyclohexene, or cyclopentene with an alpha,beta-unsaturated carboxylic acid such as acrylic acid or crotonic acid does not inherently make the ester by-product (e.g., cycloheptyl crotonate, cyclohexyl crotonate, or cyclopentyl crotonate, respectively) reported by Conia et al., Rand and Dolinski, and others using PPA or $P_2O_5$/PPA mixture.

The invention claimed is:

1. A method of synthesizing a substituted cyclopentenone compound, the method comprising (A) contacting a compound of formula (1) ("compound (1)"):

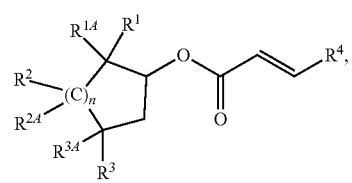

(1)

wherein subscript n is 1, 2, 3, or 4; and each of groups R1, R2, R3, and R4 is independently H or ($C_1$-$C_4$)alkyl, or any two adjacent R1 to R3 groups are bonded together to form a ($C_1$-$C_4$)alkylene and the remaining group of R1 to R3 is H or ($C_1$-$C_4$)alkyl, with an effective amount of a phosphorous pentoxide/methanesulfonic acid reagent ($P_2O_5/H_3CSO_3H$ reagent) and under reaction conditions sufficient to make a compound of formula (2) ("compound (2)"):

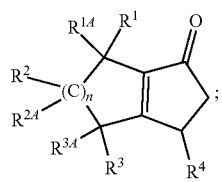

wherein subscript n and groups R1 to R4 are as defined above; and with the proviso that the contacting step (A) is free of added polyphosphoric acid (PPA).

2. The method of claim 1 wherein the ratio of $P_2O_5$ to $H_3CSO_3H$ used to make the $P_2O_5/H_3CSO_3H$ reagent is from 0.05/1 to 1/1 (weight/weight).

3. The method of claim 1, wherein the ratio of $P_2O_5$ to $H_3CSO_3H$ used to make the $P_2O_5/H_3CSO_3H$ reagent is 0.1/1 (weight/weight).

4. The method of claim 1, characterized by any one of limitations (i) to (xxi): (i) wherein at least one of R1 to R3 is a $(C_1-C_4)$alkyl or R4 is H; (ii) wherein each of R1 to R4 is H; (iii) wherein each of R1 to R3 is H and R4 is methyl; (iv) wherein each of R1 and R2 is H and each of R3 and R4 is methyl; (v) wherein R1 and/or R2 is methyl and R3 is H; (vi) wherein R1 is methyl, R2 is 1-methylethyl, and R3 is H; (vii) wherein R1 is 1-methylethyl, R2 is methyl, and R3 is H; (viii) wherein R1 and R2 independently are $(C_1-C_4)$alkyl, R3 is H, and the stereochemistry of the carbon atom bonded to R1 is (R) and the stereochemistry to the carbon atom bonded to R2 is (S); (ix) wherein R1 and R2 independently are $(C_1-C_4)$alkyl, R3 is H, and the stereochemistry of the carbon atom bonded to R1 is (S) and the stereochemistry to the carbon atom bonded to R2 is (R); (x) both (vi) and (viii); (xi) both (vi) and (ix); (xii) both (vii) and (viii); (xiii) both (vii) and (ix); (xiv) wherein R5 is H; (xv) wherein R5 is methyl; (xvi) both (i) and (xiv) or (xv); (xvii) both (ii) and (xiv) or (xv); (xviii) both (iii) and (xiv) or (xv); (xix) both (iv) and (xiv) or (xv); (xx) both (v) and (xiv) or (xv); and (xxi) any two adjacent R1 to R3 groups are bonded together to form a $(C_1-C_4)$alkylene and the remaining group of R1 to R3 is H or $(C_1-C_4)$alkyl.

5. The method of claim 1, wherein the compound (2) is selected from the group consisting of any one of compounds (2a) to (2e):

compound (2a) 2,3,4,5,6,7-hexahydro-3-methyl-1H-inden-1-one, having structure (2a):

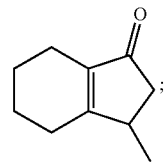

compound (2b) bicyclo[3.3.0]-1(5)-octen-2-one, having structure (2b):

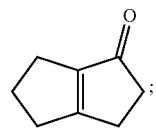

compound (2c) 4-methyl-bicyclo[3.3.0]-1(5)-octen-2-one, having structure (2c):

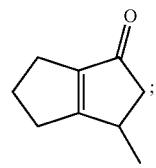

compound (2d) 10-methyl-bicyclo[5.3.0]-1(7)-decen-8-one; and compound (2e) 2,4,6,11-tetramethyl-bicyclo[6.3.0]-1(8)-undecen-9-one.

* * * * *